United States Patent [19]

Motta

[11] Patent Number: 5,032,117

[45] Date of Patent: Jul. 16, 1991

[54] TANDEM SYRINGE

[76] Inventor: Louis J. Motta, 14501 Tupper St., Ste. 60, Panorama City, Calif. 91402

[21] Appl. No.: 303,454

[22] Filed: Jan. 30, 1989

[51] Int. Cl.⁵ .............................................. A61M 37/00
[52] U.S. Cl. ...................................... 604/88; 604/187; 604/191; 604/218; 604/220; 604/246
[58] Field of Search ................... 604/86, 87, 88, 187, 604/191, 218, 220-222, 246, 255, 80

[56] References Cited

U.S. PATENT DOCUMENTS

| | | | |
|---|---|---|---|
| 657,440 | 9/1900 | McCaw | 604/191 |
| 1,234,582 | 7/1917 | Trueblood | 604/191 |
| 2,866,457 | 12/1958 | Moore | 128/214 |
| 2,939,459 | 6/1960 | Lazarte et al. | 128/218 |
| 3,401,692 | 9/1968 | Harris | 604/221 |
| 4,059,109 | 11/1977 | Tischlinger | 128/218 |
| 4,171,698 | 1/1979 | Genese | 604/88 |
| 4,313,440 | 2/1982 | Ashley | 128/218 |
| 4,424,057 | 1/1984 | House | 604/88 |
| 4,465,476 | 8/1984 | Gähwiler | 604/191 |
| 4,516,969 | 5/1985 | Kintner | 604/187 |
| 4,581,016 | 4/1986 | Gettig | 604/88 |
| 4,642,102 | 2/1987 | Ohmori | 604/210 |
| 4,685,910 | 8/1987 | Schweizer | 604/218 |
| 4,693,706 | 9/1987 | Ennis | 604/87 |
| 4,702,737 | 10/1987 | Pizzino | 604/191 |
| 4,772,273 | 9/1988 | Alchas | 604/218 |

FOREIGN PATENT DOCUMENTS 558915 3/1957 Italy ................................ 604/191

OTHER PUBLICATIONS

Akers, et al., "Intravenous Drug Delivery Primer", American Journal of Hospital Pharmacy, vol. 44, pp. 2528-2533, Nov., 1987.

Primary Examiner—C. Fred Rosenbaum
Assistant Examiner—Mark O. Polutta
Attorney, Agent, or Firm—Don C. Lawrence; Gene W. Arant

[57] ABSTRACT

A syringe for the gravity-feed intravenous administration of drugs and the like comprises three hollow, elongated, cylindrical, outer, middle and inner barrels nested concentrically and tandemly within each other and means for suspending the syringe above a patient. The middle barrel has an open end with a rubber stopper on it slidably and sealingly disposed within the outer barrel to adjustably define a liquid-receiving volume therein. The inner barrel has a hollow interior, an open external end containing a microbial filter through which its interior is vented to ambient pressure, and a closed end having a sharp, hollow needle communicating with the interior and extending outwardly therefrom. Selective advancement of the inner barrel toward the rubber stopper causes the needle to penetrate the stopper and vent the volume to ambient pressure through the interior of the inner barrel and the filter, whereby liquid medication in the volume may gravity-feed through an established primary or secondary I.V. set to the patient.

20 Claims, 2 Drawing Sheets

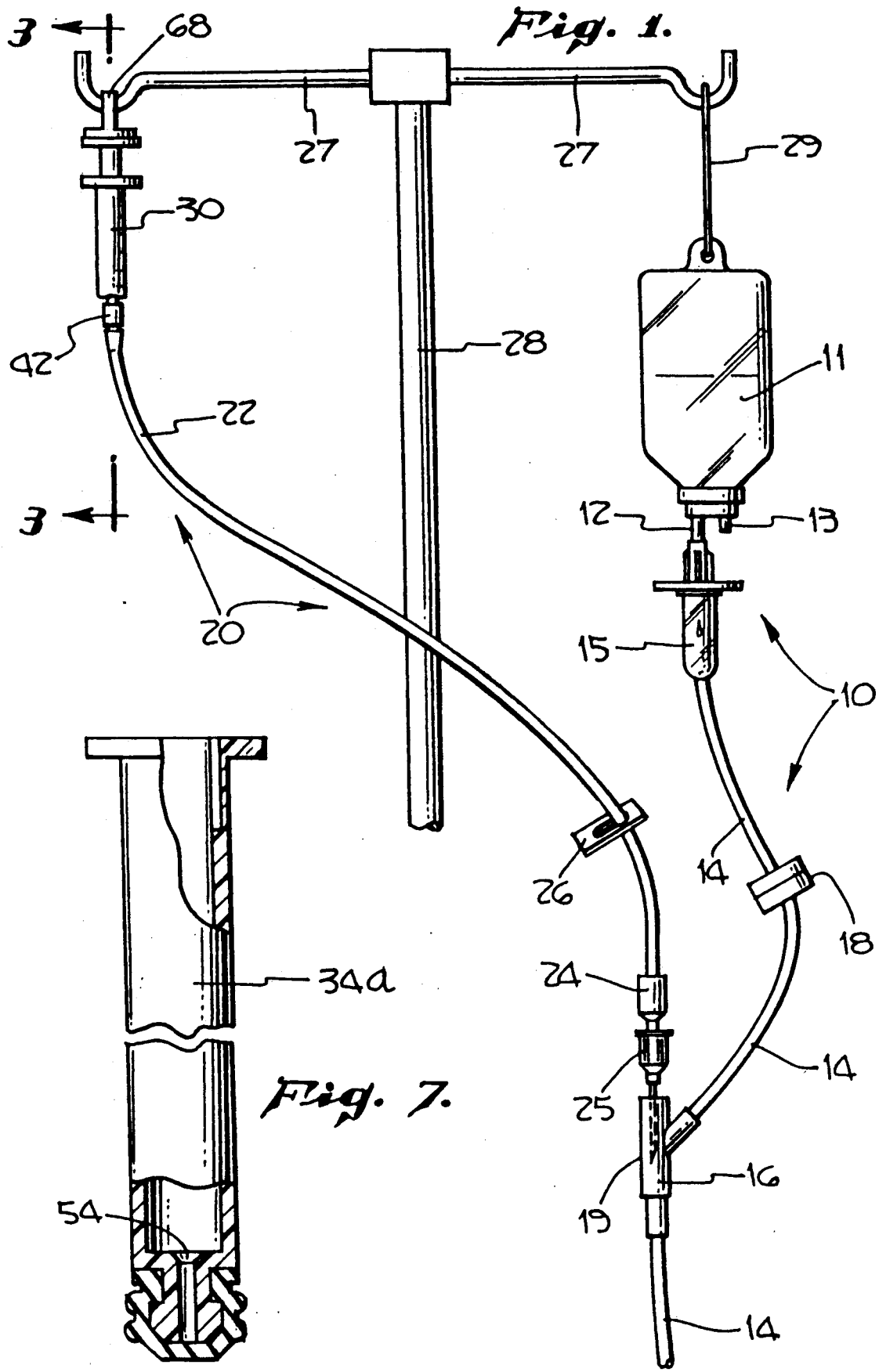

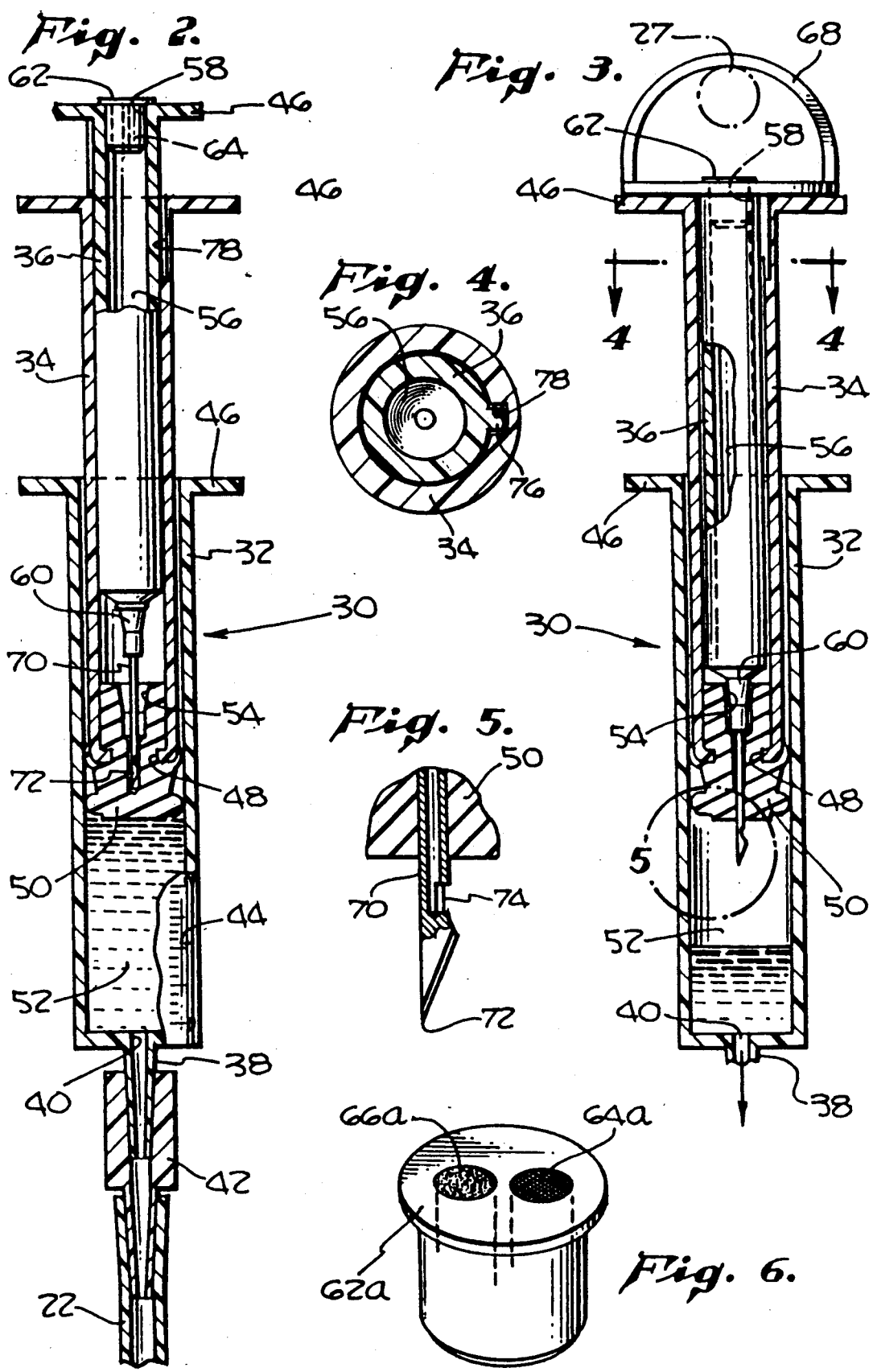

TANDEM SYRINGE

BACKGROUND

1. Field of the Invention

This invention pertains, in general, to medical devices, and in particular, to a tandem syringe for the gravity-feed, intravenous administration of parenteral liquids, such as medications and the like, and the method of its use.

2. Description of the Related Art

The intravenous ("I.V.") administration of drugs has increased dramatically over the past decade and approximately 40% of all drugs and fluids delivered to patients in hospitals today are administered intravenously.[1]

[1]. M. J. Akers, et al., "Intravenous Drug Delivery Primer," *American Journal of Hospital Pharmacy, Vol.* 44, p.2528, et seq., Nov. 1987.

Over the years, a wide variety of devices and methods have been developed to assist the health care practitioner in the I.V. delivery of fluids and medicaments. These systems may be broadly catagorized into those which accomplish their function immediately or contemporaneously, and those which achieve delivery intermittently or continuously over an extended period of time. They may be further grouped between those which achieve delivery by means of a "push," or positively-applied force acting on the fluid, and those which are gravity-feed.

An example of device which can accomplish I.V. delivery either immediately or intermittantly by means of a "push" is the well-known hypodermic syringe, which comprises a hollow barrel having a with a needle on it and a sliding piston plunger within. Typically, the syringe is used both to withdraw the liquid medication from a supply vial and to inject it subcutaneously and/or intravenously through the agency of the same needle by means of an immediate "push" supplied manually by the health practitioner, or intermittently or continuously over a period of time by the use of an associated battery- or spring-operated syringe pump.

Examples of "tandem" syringes having specialized functions, such as the push delivery of dual dosages of drugs, may be found in patents to J. L. Pizzino (U.S. Pat. No. 4,702,737), S. J. Ashley (U.S. Pat. No. 4,313,440), and J. A. Lazarte, et al. (U.S. Pat. No. 2,939,459). E. A. Tischlinger, in U.S. Pat. No. 4,059,109, and W. A. Gettig, in U.S. Pat. No. 4,581,016, each describe another type of syringe capable of mixing a diluent with a dry medication prior to its injection. In U.S. Pat. No. 4,685,910, R. J. Schweizer describes a type of syringe capable of delivering secondary fluids within a primary I.V. administration set utilizing a peristaltic infusion pump.

An example of apparatus typically utilized for gravity-feed of parenteral fluids is found in a patent to R. C. Moore, U.S. Pat. No. 2,866,457. Such systems typically comprise a relatively large container, usually a flexible plastic bag, of a primary parenteral fluid which is suspended above the patient to generate a pressure head greater than the the vasopressure of the patient, along with a length of flexible tubing terminating in an indwelling venocatheter. Intermediate the container and the catheter are typically found a check valve, a flow-control/shutoff clamp, and more proximal to the patient, a Y-connector which may be used to administer, either by push or gravity-feed, a secondary fluid in the "piggyback" fashion described below.

Gravity-feed I.V. delivery systems almost always are of the catagory which operate intermittantly or continuously over a period of time, as opposed to immediately. A detailed overview of various types of such intermittent I.V. systems, along with their attendent characteristics and problems, is provided by R. P. Rapp.[2]

[2]. R. P. Rapp, "Considering product features and costs in selecting a system for intermittent I.V. drug delivery," *Am. J. Hosp. Pharm.*, Vol.44, pp.1381-91.

It is occasionally desirable to administer a small, secondary dose of medication intermittantly or continuously over an interval of time to a patient to whom a primary I.V. set is already connected. This is presently accomplished by "piggybacking" a "minibag" containing the medication onto the primary system and delivering it through the same venipuncture utilized by the primary system.

In such a procedure, the dose is typically withdrawn from the supply vial using a conventional disposable hypodermic syringe in the manner described above and then injected with that same syringe into a small, sterile, plastic "minibag". The dose may be diluted with a larger quantity of the primary parenteral fluid or other diluent in the same manner. The minibag of solution is then suspended above the container of the primary set and connected through a secondary I.V. set to an entry port on the primary set's Y-connector. The higher pressure head in the minibag causes a check valve in the primary set to close and shut off flow of the primary fluid, and secondary infusion is accomplished from the minibag by gravity-feed.

The minibags used in the above-described procedure are relatively expensive, and it would be more cost effective if the same disposable syringe which was used to measure and withdraw the medication from the supply vial could be used to gravity-feed the medication. A gravity-feed syringe system which is said to achieve this end is described by R. P. Rapp,[3] and comprises a conventional disposable syringe which is suspended by means of plastic bag after it is filled and connected to the patient or primary set by means of a secondary set which includes a special vented fitting.

[3]. Id., at p. 2535.

Unfortunately, the special vent fittings used by this system are relatively expensive and are occasionally unreliable because they vent the syringe through the Luer-lock-type fitting at its bottom, and the medication can backflow through the vent by gravity and inadvertently shut off flow through the system.

It is therefore desirable to provide a gravity-feed I.V. delivery system in which the same device is capable both of withdrawing and measuring a small-to-medium dose of a liquid medication from a conventional supply vial, and reliably administering the dose to the patient through a conventional primary or secondary I.V. set, and which may be cost-effectively disposed of thereafter. These objects and others are achieved in the tandem syringe of the present invention.

SUMMARY OF THE INVENTION

The syringe of the present invention comprises three hollow, elongated, cylindrical barrels, including an outer, a middle and an inner barrel, all of which are nested concentrically and tandemly within each other.

The outer barrel is made of a clear plastic and has measurement markings and a tip with a Luer-lock-type fitting on it.

The middle barrel has an open end with a rubber stopper on it which is sealingly slidable within the outer barrel to adjustably define a liquid-medication-receiving volume therein.

The inner barrel has a hollow interior, an open external end which contains a microbial filter through which the interior of the barrel is vented to ambient pressure, and a closed end slidably received within the middle barrel. A sharp, hollow needle communicates with the interior of the inner barrel through its closed end and extends outwardly therefrom toward the stopper.

Selective advancement of the inner barrel toward the rubber stopper causes the needle to penetrate the stopper and vent the top of the volume to ambient pressure through the inner barrel and filter, whereby liquid medication in the volume may gravity-feed through an established primary or secondary I.V. set to the patient.

Preferably, a lock in the form of a key and corresponding keyway are provided on respective ones of the inner and middle barrels to prevent inadvertent advancement of the former into the latter and resultant penetration of the stopper.

Means are provided for suspending the syringe from a pole or stand, and in a preferred embodiment, consist of a thumb-loop molded on the external end of the inner barrel.

A better understanding of the syringe of the present invention, its method of use, and its many attendent advantages may be had from a consideration of the following detailed description of its preferred embodiments and the accompanying drawings thereof, a brief description of which now follows.

BRIEF DESCRIPTIONS OF THE DRAWINGS

FIG. 1 is a partial elevational view of a gravity-feed I.V. drug delivery system which includes a primary set and a secondary set incoporating the tandem syringe of the present invention;

FIG. 2 is an enlarged longitudinal cross-sectional view through an embodiment of the syringe of the present invention;

FIG. 3 is an enlarged longitudinal cross-sectional view through the syringe shown in FIG. 1, as revealed by the section taken therein along the line 3—3;

FIG. 4 is an enlarged lateral cross-section view through the syringe shown in FIG.3, as revealed by the section taken therein along the line 4—4;

FIG. 5 is an enlarged cross-sectional detail of an embodiment of a vented needle used in the syringe shown in FIG. 3, as revealed by the detail 5 taken therein;

FIG. 6 is an enlarged isometric view of a filter cap in one embodiment of the syringe; and FIG. 7 is partial longitudinal cross-sectional view of an alternative embodiment of the middle barrel of the syringe of the present invention.

DESCRIPTION OF THE PREFERRED EMBODIMENTS

FIG. 1 illustrates a gravity-feed I.V. drug administration system of a type with which the tandem syringe of the present invention may be used efficaciously. The system illustrated therein comprises a primary delivery system 10 and a secondary system 20.

The primary system 10 comprises a large container 11 of primary liquid parenteral I.V. infusion material. The container may be in the form of an unvented flexible plastic bag with an outlet 12 and an optional injection port 13 of penetrable rubber through which drugs or other materials may be injected directly into the primary I.V. fluid.

The primary system 10 also includes a primary I.V. tubing set, which typically comprises a length of flexible tubing 14 connected at its distal end to the container 11 by means of a drip chamber 15 attached to the container's outlet 12, and at its proximal end to the patient through a venous catheter (not illustrated).

Intermediate of the two ends of the tubing 14 are a Y-connector 16 proximal to the patient and a check valve 18 distal thereof. The check valve 18 prevents flow therethrough when the pressure of the fluid below it exceeds the pressure of that above it. The Y-connector includes an entry port 19 for the introduction of the secondary delivery system 20. A flow control device in the form of a roller clamp (not illustrated) is usually included in the primary set to control the rate of fluid flow to the patient.

The secondary system 20 illustrated comprises a secondary tubing set, which includes a second length of tubing 22 which is connected at its proximal end to the entry port 19 of the Y-connector 16 by means of a male fitting 24 or a hypodermic needle 25. At its distal end, the secondary set is connected to the container from which it is desired to infuse a secondary drug or liquid, and in the prior art, this container typically comprises a minibag (not illustrated) of the type described hereinabove. The secondary set may also include a shutoff or roller clamp 26 for flow control.

Both the primary system 10 and the secondary system 20 are suspended above the patient by means of the arms 27 of an I.V. pole or stand 28, and suspension may involve the use of a hangar 29 to achieve the height difference between the primary and secondary containers necessary to shut the check valve 18 and initiate secondary flow.

In the system illustrated in FIG. 1, the container for the secondary fluid comprises the tandem syringe 30 of the present invention. A better understanding of this syringe and its operation may be had from a consideration of the more detailed views therof provided in FIGS. 2-7.

Referring in particular to FIG. 2, a preferred embodiment of the syringe 30 of the present invention illustrated therein comprises three hollow, elongated, cylindrical barrels, including an outer barrel 32, a middle barrel 34, and an inner barrel 36. The barrels are nested concentrically and tandemly within one another to define a pair of tandem syringes in which the middle barrel 34 comprises the plunger of one syringe and the inner barrel 36 comprises the plunger of a second.

The outer barrel 32 includes a tip 38 through which an opening 40 extends outwardly from the interior of the barrel. The tip 38 is configured externally to conform to a male Luer-lock-type fitting to facilitate its connection to a hypodermic needle or female adapter 42 of that type. In the preferred embodiment illustrated, the outer barrel is molded from a clear or translucent plastic for visibility, and includes volumetric graduations or markings 44 to facilitate the measurement of the volume of liquid medication to be administered. The outer barrel also preferably includes a pair of finger flanges 46 for manual gripping, as do the other barrels 34 and 36.

The middle barrel 34 has an open end 48 with a penetrable rubber diaphragm, or stopper, 50 fitted on it which is sized to be sealingly slidable in the distal direction within the outer barrel and to define an adjustable, liquid-medication-receiving volume or chamber 52 therein and, with the aid of the vacuum created thereby, draw that volume of medication into the chamber through a hypodermic needle fitted on the tip 38 from a supply vial, in the same manner as a conventional hypodermic syringe is loaded.

The stopper 50 may be molded to include a ramped needle guide 54 or, as illustrated in an alternative embodiment of the middle barrel 34a illustrated in FIG. 7, this feature may be molded into the open end of the barrel itself.

The inner barrel 36 has a hollow interior 56, an open external end 58, and a closed internal end 60. Sealingly fitted into the open end of the inner barrel is a cap or plug 62 which contains a microbial air filter 64 capable of filtering out particulate matter as small as from about 0.22 to about 0.45 microns in size, and through which the interior of the barrel is always vented to ambient pressure.

An alternative embodiment of the plug 62a is illustrated in the enlarged isometric view of FIG. 6, in which a penetrable rubber needle port 66a is disposed adjacent to the filter 64a to permit, for example, a second tandem syringe to be piggybacked onto the one illustrated.

In the embodiment illustrated in the figures, means for suspending the syringe from the arm 27 of an I.V. pole are provided in the form of an enlarged thumb-loop 68, which is molded onto the external end of the inner barrel. Alternatively, these means can take the form of a simple plastic strap having an aperture in either end, one of which is slipped around the outer barrel and the other of which is slipped over the arm of the stand.

The closed end 60 of the inner barrel 36 is slidably received within the middle barrel 34, and a hollow needle 70, which has a sharp end 72 on it, communicates with the interior 56 of the inner barrel through the closed end and extends proximally outward therefrom and toward the stopper 50.

In the preferred embodiment illustrated in FIG. 5, the needle 70 is a vented, bayonet-type needle, so-called because it includes a closed, slicing type of sharp end 72 and is vented through a lateral aperture 74 through the sidewall of the needle adjacent to the end. This form of needle prevents the possibility of "coring" of the rubber stopper, especially by a larger size of needle. The sharp end of the needle may, to the same effect, be conical in shape, like a football inflation needle, provided it is sharp and closed. In a preferred embodiment in which the needle is steel, the needle is molded into the end of the plastic inner barrel, and more preferably, is molded of plastic along with the inner barrel as a single piece.

To prevent inadvertent penetration of the stopper by the needle, the inner barrel is provided with a key 76 which is sized to prevent proximal movement of the barrel within the middle barrel so long as the key is misaligned with a corresponding keyway 78 formed in the middle barrel, which is the configuration of the syringe illustrated in FIG. 2. When penetration and venting are desired, the inner barrel is rotated within the middle barrel until the key is aligned with the keyway and the inner barrel is slid proximally as far as it will go, causing the tip of the needle to penetrate the stopper and vent the contents of the medication chamber 52 to atmospheric pressure, whereby the medication may flow by gravity out the tip of the syringe and in the direction of the arrow illustrated in FIG. 3.

The method of use of the syringe of the present invention is fairly straightforward. In one such method, the syringe is provided sterile and empty in a sterilized tearaway bag. A conventional hypodermic needle is fitted to its tip and used to draw the desired volumetric dose of medication into the chamber, as described above. The needle is then removed and the tip of the syringe is connected to the input fitting of either a conventional primary or secondary I.V. tubing set, depending on whether the fluid is to be administered as a primary fluid or as a secondary fluid piggybacked onto an established primary set.

The syringe is then suspended above the patient and, if used as a secondary system, at a position higher than the primary fluid container. The proximal end of the set is connected to the patient or an input port on the primary system's Y-connector.

When it is desired to commence flow of the system, the key is aligned with the keyway and the inner barrel advanced proximally until the needle penetrates the stopper and vents the chamber, at which point flow commences, as described above.

By now, skilled practitioners will recognize that other modifications may be made in the materials, construction, and method of use of the tandem syringe disclosed herein. For example, it is feasible to provide respective ones of the outer and inner surfaces of the inner and middle barrels with mating screw threads such that, with rotation of the inner barrel within the outer, the inner barrel is caused to advance proximally therein, and is prevented thereby from doing so otherwise.

Likewise, the syringe may be provided preloaded and capped for refrigerated or frozen storage for extended periods before I.V. delivery to the patient. Alternatively, the the syringe can be supplied preloaded with a dry medication in solute form and stored for long periods, then used both to mix the medication with a liquid solvent and then administer it to a patient.

Other variations and modifications will suggest themselves, depending upon the particular application at hand. Accordingly, the scope of the present invention should be limited only be the claims appended hereafter.

What is claimed is:

1. A tandem syringe, gravity-feed, intravenous drug delivery system, comprising:

first and second syringes, each comprising a barrel and a moveable plunger, the barrel of the second syringe being disposed tandemly within the barrel of the first to comprise its plunger and being slidably and sealingly moveable therein to define an adjustable, fluid-receiving volume therein, the barrel of the second syringe having an internal end with an opening through it communicating between the volume and ambient pressure and a penetrable diaphragm across the opening to seal it off, the plunger of the second syringe having means associated with it for selectably penetrating the diaphragm and venting the volume to ambient pressure therethrough.

2. The delivery system of claim 1, wherein the means for selectably penetrating the diaphragm and venting the volume to ambient pressure further comprise:

the plunger of the second syringe having a hollow interior, an external end with an opening through it for venting the interior of the plunger to ambient pressure, and a closed internal end with a sharp, hollow needle extending through it and spaced apart from the diaphragm and disposed to pierce the diaphragm with movement of the plunger toward it, thereby venting the volume through the needle to the interior of the plunger.

3. The delivery system of claim 2, wherein the means for selectably penetrating the diaphragm and venting the volume to ambient pressure further include means for preventing inadvertent venting of the diaphragm, comprising:

a key and corresponding keyway formed in respective ones of the plunger and barrel of the second syringe, the plunger being rotatable within the barrel and the key being disposed to prevent movement of the plunger toward the diaphragm absent alignment of the key with the keyway.

4. The delivery system of claim 2, wherein the needle further comprises a closed-ended, side-vented needle.

5. The delivery system of claim 2, wherein the plunger of the second syringe and the needle are molded from plastic as a single piece.

6. The delivery system of claim 2, wherein the interior of the plunger of the second syringe is vented to ambient pressure through a microbial filter disposed in the external end of the plunger.

7. The delivery system of claim 1, wherein the barrel of the first syringe further includes a tip with an opening into the volume and means for connecting the opening to the inlet fitting of a primary or secondary I.V. infusion set.

8. The delivery system of claim 1, further comprising means for suspending the system from a stand or hanger.

9. The delivery system of claim 8, wherein the means for suspending the system further comprise a loop formed on the external end of the plunger of the second syringe.

10. The delivery system of claim 2, wherein the external end of the plunger of the second syringe further includes a rubber port to permit a hypodermic needle to be inserted therethrough and into the interior of the plunger.

11. A device for gravity-feed intravenous delivery of liquid medications, comprising:

an elongated first cylindrical outer barrel made of translucent material and having a closed proximal end and an open distal end, said proximal end having a tip with a Luer-lock-type fitting thereon and an opening extending therethrough and into the barrel;

a second cylindrical middle barrel having an open proximal end slidably disposed concentrically within said first barrel and an open distal end extending distally and externally therefrom, said proximal end having resilient stopper means associated therewith for: forming a sliding seal between said first and second barrels, for defining an adjustable, fluid-receiving volume proximal thereof within said first barrel with distal movement of said second barrel within said first barrel, and for isolating said volume from ambient pressure at a distal end thereof; and a third cylindrical inner barrel having a hollow interior, a closed proximal end slidably disposed concentrically within said second barrel, and an open distal end extending distally and externally therefrom, said open end having an air filter fitted therein whereby ambient air entering said interior through said end is filtered of microbes, said closed end having a hollow needle extending therethrough with a sharp proximal end thereon spaced apart from said stopper means such that elective proximal movement of said third barrel within said second barrel causes said needle to penetrate said stopper means and vent said volume to ambient pressure through said interior of said third barrel, whereby fluid medication contained within said volume is permitted to flow with gravity through said tip.

12. The device of claim 11, wherein said filter is capable of filtering out particulate matter larger than from about 0.22 to 0.45 microns in size.

13. The device of claim 11, wherein said third barrel has a thumb strap disposed on said open end thereof for hanging said device from a stand or a hanger.

14. The device of claim 11, wherein said needle and said third barrel are molded from a plastic material as a single piece.

15. The device of claim 11, wherein said sharp end of said hollow needle is closed, and said needle further includes a lateral vent opening through a sidewall thereof adjacent to said closed opening.

16. The device of claim 11, further including means for electively advancing said third barrel in the proximal direction within said second barrel and penetrating said stopper means with said needle, comprising:

corresponding threads formed on respective ones of an interior surface of said second barrel and an exterior surface of said third barrel and engaged with each other such that rotation of said third barrel about a longitudinal axis and relative to said second barrel advances said third barrel rapidly therein in the proximal direction.

17. The device of claim 11, wherein said open end of said third barrel further includes a rubber hypodermic needle entry port adjacent to said air filter.

18. The device of claim 11, further comprising:

a length of flexible tubing having a pair of ends, a Luer-lock-type input fitting disposed on one of said ends and connected to said tip, a Luer-lock-type output fitting disposed at the other of said ends, and a shutoff clamp thereon disposed between said ends.

19. A piggyback method for intermittent gravity-feed intravenous administration of liquid medication to a patient having a primary I.V. set in place using a syringe of the type which includes a barrel and hollow first and second plungers nested tandemly within it, the first plunger having an open end sealed by a penetrable stopper thereon slidably disposed within the barrel to define the top of a selectively adjustable chamber therein, the second plunger having an open end vented to ambient pressure through a microbial filter and a closed end slidably disposed within the first plunger with a sharp, hollow needle extending outwardly therefrom adjacent to the stopper, comprising the steps of:

attaching a sterile hypodermic needle to the syringe;

inserting the needle through the stopper of a vial of the liquid medication desired to be administered and withdrawing the first plunger from the syringe until the desired volume of the medication is drawn into the chamber of the syringe;

removing the hypodermic needle from the syringe and connecting the syringe to the inlet of a secondary I.V. set;

connecting the outlet of the secondary set to an inlet of a Y-fitting contained in the primary set;

suspending the syringe above the parenteral fluid container of the primary set; and advancing the second plunger within the first plunger until the needle penetrates the stopper, thereby venting the top of the chamber of liquid medication to atmospheric pressure through the microbial filter.

20. The method of claim 19, wherein the syringe additionally includes means for locking the second plunger against inadvertent advancement within the first plunger, comprising the further step of:

unlocking the second plunger for advancement within the first plunger.

* * * * *